US009295591B2

(12) United States Patent
Takahashi

(10) Patent No.: US 9,295,591 B2
(45) Date of Patent: Mar. 29, 2016

(54) METHOD OF MANUFACTURING DISPOSABLE DIAPER

(71) Applicant: LIVEDO CORPORATION, Ehime (JP)

(72) Inventor: Yuki Takahashi, Tokushima (JP)

(73) Assignee: LIVEDO CORPORATION, Ehime (JP)

( * ) Notice: Subject to any disclaimer, the term of this patent is extended or adjusted under 35 U.S.C. 154(b) by 0 days.

(21) Appl. No.: 14/210,842

(22) Filed: Mar. 14, 2014

(65) Prior Publication Data

US 2014/0299267 A1    Oct. 9, 2014

Related U.S. Application Data

(60) Provisional application No. 61/807,842, filed on Apr. 3, 2013.

(51) Int. Cl.
*A61F 13/15* (2006.01)
*B32B 37/12* (2006.01)

(52) U.S. Cl.
CPC ..... *A61F 13/15699* (2013.01); *A61F 13/15772* (2013.01); *A61F 2013/1591* (2013.01); *B32B 37/1292* (2013.01); *Y10T 156/1062* (2015.01); *Y10T 156/1084* (2015.01); *Y10T 156/1085* (2015.01); *Y10T 156/1304* (2015.01)

(58) Field of Classification Search
CPC ............... A61F 2013/1591; B32B 37/1292
See application file for complete search history.

(56) References Cited

U.S. PATENT DOCUMENTS 4,874,451 A  *  10/1989  Boger et al. ............ 156/291

FOREIGN PATENT DOCUMENTS

| JP | 06-197925 A | 7/1994 |
| JP | 2006-141642 A | 6/2006 |
| JP | 2010-142500 A | 7/2010 |

OTHER PUBLICATIONS

Notification of Reason(s) for Refusal for Japanese Patent App. No. 2012-063086 (Dec. 8, 2015) with English translation.

* cited by examiner

*Primary Examiner* — Linda L Gray
(74) *Attorney, Agent, or Firm* — Cermak Nakajima & McGowan LLP; Tomoko Nakajima

(57) ABSTRACT

An adhesive is independently ejected from a plurality of ejecting sections to an outer layer nonwoven fabric continuum conveyed in a conveyance direction. At this time, the adhesive is ejected to three partial regions, of an opening portion formation region in which an opening portion is formed, which are divided by two straight lines passing an inside of the opening portion formation region from the ejecting sections corresponding to the partial regions. Further, when ejection of the adhesive from the ejecting section is stopped, an adhesive non-application region is formed in the inner partial region held between the outermost two partial regions of the three partial regions.

3 Claims, 7 Drawing Sheets

F I G. 2
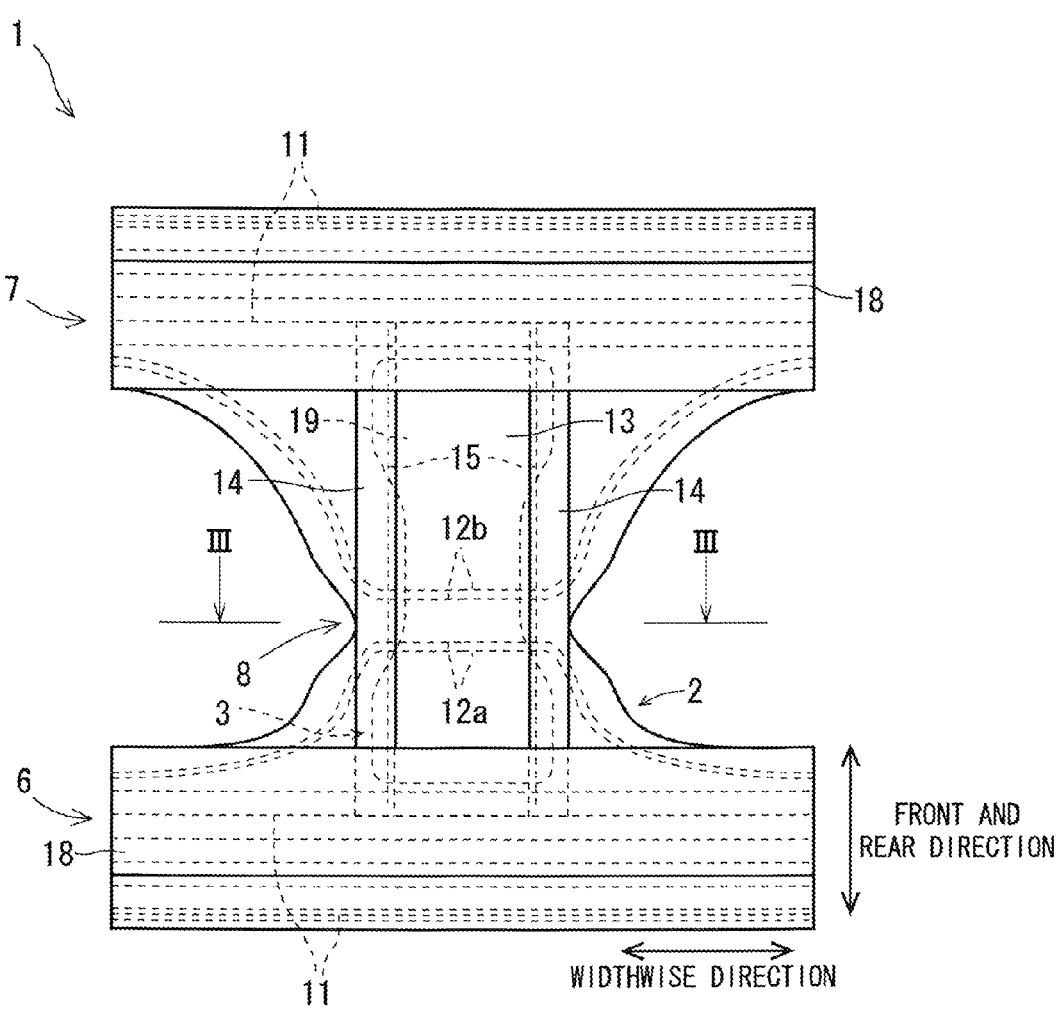

F I G. 3
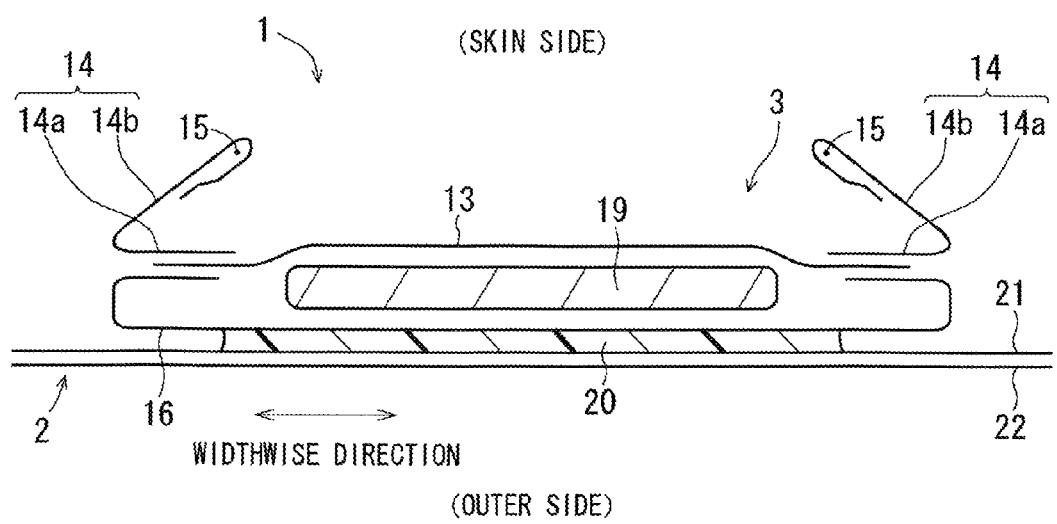

F I G . 5
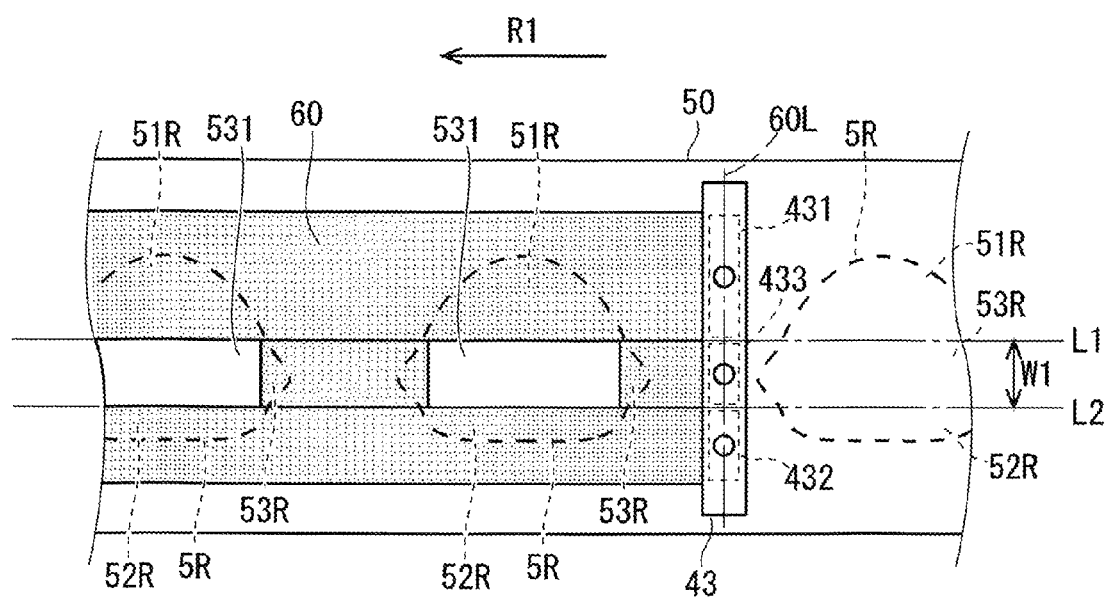

METHOD OF MANUFACTURING DISPOSABLE DIAPER

BACKGROUND OF THE INVENTION

1. Field of the Invention

The present invention relates to a method of manufacturing a disposable diaper, and particularly to a technology to apply an adhesive for bonding between sheets.

2. Description of the Background Art

Conventionally, a disposable diaper is structured by a laminate of a nonwoven outer layer sheet and a nonwoven inner layer sheet, and includes a main body portion provided with leg insertion opening portions which serve as leg insertion portions for inserting a leg. In a manufacturing process of such a disposable diaper, for example, after an adhesive is applied to one of an outer layer sheet and an inner layer sheet extending in a strip shape, the sheets are superimposed and bonded, thereby forming a sheet-like base material. Then, after an absorbent body or the like is attached to this sheet-like base material, opening portions serving as leg insertion opening portions are formed by a cutter, and the sheet-like base material is further separated into individual disposable diapers (for example, Japanese Patent Application Laid-Open No. 2010-142500).

However, in case of the conventional manufacturing method, since the adhesive is also applied to portions cut out for forming the opening portions, loss of the adhesive is generated. Accordingly, it is desirable that the adhesive application be restrictively performed on the opening portions. However, the concrete solution is little known.

SUMMARY OF THE INVENTION

The present invention is directed toward a method of manufacturing a disposable diaper.

A method of manufacturing a disposable diaper according to a first aspect, including: (a) a step of conveying a first sheet in a predetermined conveyance direction; (b) a step of independently ejecting an adhesive from a plurality of ejecting sections and applying the adhesive to the first sheet conveyed in the (a) step; (c) a step of adhering a second sheet to a surface of the first sheet, to which the adhesive has been applied in the (b) step, and forming a sheet-like base material; and (d) a step of cutting the sheet-like base material and forming an opening portion, wherein in the (b) step, the adhesive is ejected to three or more partial regions, of an opening portion formation region in which the opening portion is formed, which are divided by at least two or more straight lines passing an inside of the opening portion formation region from the ejecting sections corresponding to the partial regions, and when ejection of the adhesive from the ejecting sections is stopped, an adhesive non-application region is formed in the one or more inner partial regions held between the outermost two partial regions of the three or more partial regions.

According to the first aspect, the adhesive non-application region, to which the adhesive is not applied, is formed in the opening portion formation region. Accordingly, an amount of the adhesive which is applied to the opening portion formation region cut out as the opening portion can be reduced. Therefore, loss of the adhesive can be reduced.

Further, a second aspect is the method of manufacturing a disposable diaper according to the first aspect, wherein in the (b) step, in the outermost two partial regions of the three or more partial regions, the adhesive is continuously ejected from the ejecting sections corresponding thereto.

In accordance with the method of manufacturing a disposable diaper according to the second aspect, the adhesive is thoroughly applied to the outer partial regions. As a result, the adhesive can be reliably applied to a part of the peripheral edge portion of the opening portion formation region overlapping the outer partial regions. Therefore, cutting of this peripheral edge portion can be satisfactorily performed.

Further, a third aspect is the method of manufacturing a disposable diaper according to the first or second aspect, wherein in the (b) step, the adhesive is applied linearly, spirally, or in a planar state.

In accordance with the method of manufacturing a disposable diaper according to the third aspect, since a gap appropriate for adhesion between the first sheet and the second sheet can be provided due to the linear or spiral application of the adhesive, air permeability is satisfactorily secured. Moreover, when the adhesive is applied in a planar state, the first sheet and the second sheet can be bonded uniformly.

Further, a fourth aspect is the method of manufacturing a disposable diaper according to any one of the first to third aspects, wherein in the (b) step, the adhesive is applied in such a manner that an area ratio of the adhesive non-application region to the opening portion formation region does not exceed 90%.

In accordance with the method of manufacturing a disposable diaper according to the fourth aspect, the adhesive can be satisfactorily applied to a vicinity of the peripheral edge portion.

Therefore, an object of the present invention is to provide a technology to reduce the loss of the adhesive generated in the process of manufacturing a disposable diaper.

These and other objects, features, aspects and advantages of the present invention will become more apparent from the following detailed description of the present invention when taken in conjunction with the accompanying drawings.

BRIEF DESCRIPTION OF THE DRAWINGS

FIG. 2 is a plan view of the disposable diaper illustrated in FIG. 1 in a developed state, as viewed from a skin side;

FIG. 3 is a cross-sectional view of the disposable diaper at a III-III position illustrated in FIG. 2;

FIG. 5 is a schematic top view illustrating a state in which an adhesive is applied to an outer layer nonwoven fabric continuum;

DESCRIPTION OF THE PREFERRED EMBODIMENTS

Figure 1:
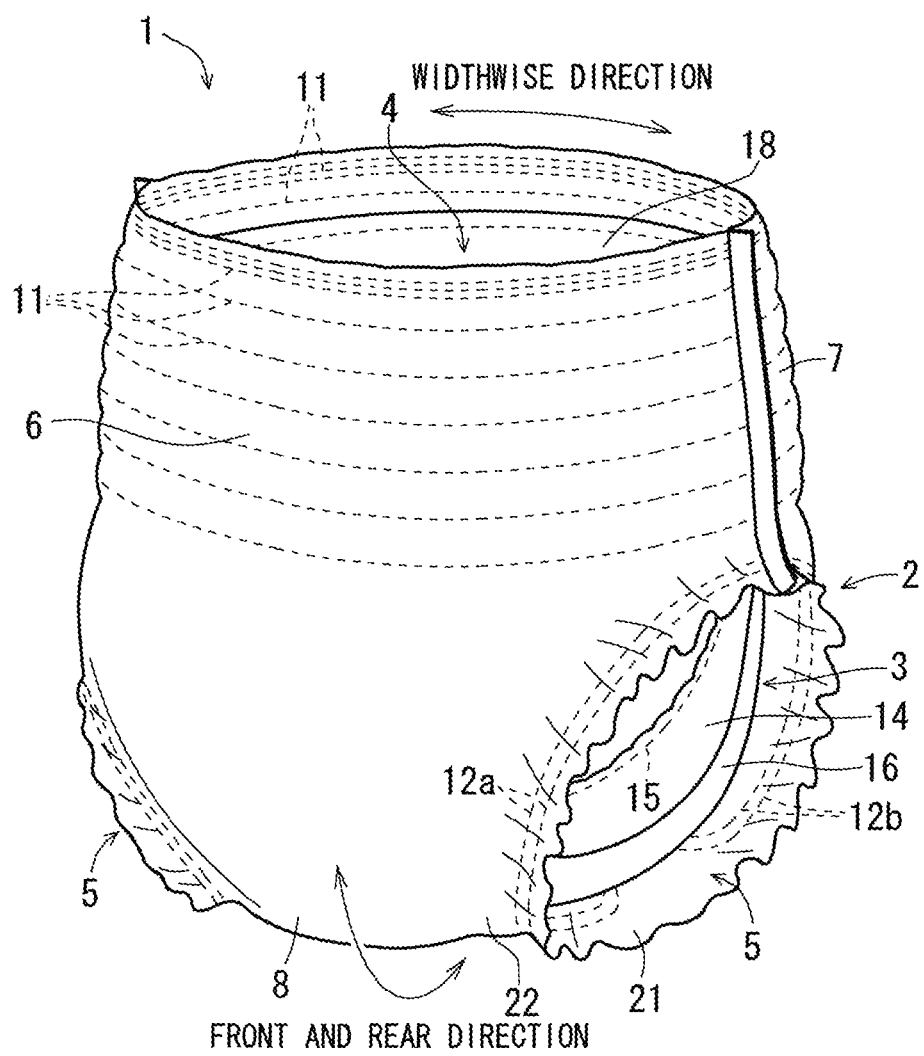
FIG. 1 is a perspective view of a disposable diaper according to a first preferred embodiment.

Referring to the drawings, the preferred embodiments will be described below in detail. However, components described in these preferred embodiments are merely examples, and it is not intended that the scope of the present invention be limited only to those. Further, in FIG. 1 and the respective drawings hereinbelow, in order to easily understand the drawings, there are cases where a size and a number of each portion are illustrated in an exaggerated or simplified manner, as necessary.

1. First Preferred Embodiment

1.1 Structure of Pants Type Disposable Diaper 1

FIG. 1 is a perspective view of a disposable diaper 1 according to a first preferred embodiment. FIG. 2 is a plan view of the disposable diaper 1 illustrated in FIG. 1 in a developed state, as viewed from a skin side. FIG. 3 is a cross-sectional view of the disposable diaper 1 at a II-II position illustrated in FIG. 2.

As illustrated in FIG. 1, the pants type disposable diaper 1 has a front waist area 6 fitted to a ventral surface of a wearer, a rear waist area 7 fitted to a back surface of the wearer, and a narrow crotch area 8 connecting the front waist area 6 and the rear waist area 7. Hereinbelow, a direction in which the front waist area 6, the crotch area 8, and the rear waist area 7 range is referred to as "front and rear direction", and a direction orthogonal to the front and rear direction and along a surface of the disposable diaper 1 is referred to as "widthwise direction".

The disposable diaper 1 includes a sheet-like exterior member 2 stretching across the front waist area 6, the crotch area 8, and the rear waist area 7, and an absorbent body 3 bonded to a surface of the exterior member 2 on the skin side in a vicinity of the crotch area 8. When wearing the disposable diaper 1, the exterior member 2 covers a waist and a crotch of the wearer. Further, the absorbent body 3 is fitted to a crotch portion of the wearer.

The exterior member 2 has an inner layer nonwoven fabric 21, an outer layer nonwoven fabric 22, and a plurality of elastic members 11, 12a, and 12b interposed between the inner layer nonwoven fabric 21 and the outer layer nonwoven fabric 22. The inner layer nonwoven fabric 21 and the outer layer nonwoven fabric 22 both extend from the front waist area 6 to the rear waist area 7 in the front and rear direction, and are narrowed in the crotch area 8 positioned between the front waist area 6 and the rear waist area 7 in the widthwise direction. Further, an outer side surface of the inner layer nonwoven fabric 21 and a skin side surface of the outer layer nonwoven fabric 22 are bonded with an adhesive. It should be noted that a hot melt adhesive of polyolefin, rubber, vinyl acetate, or the like can be used as the adhesive.

The inner layer nonwoven fabric 21 and the outer layer nonwoven fabric 22 in the present preferred embodiment are formed of water-repellent nonwoven fabrics using, for example, hydrophobic fibers (polypropylene, polyethylene, polyester, polyamide, nylon, or the like). It should be noted that a plastic film may be used instead of the inner layer nonwoven fabric 21 and the outer layer nonwoven fabric 22.

Upon wearing, both side portions of the front waist area 6 and both side portions of the rear waist area 7 are bonded to each other. Specifically, in a vicinity of right and left hip portions of the wearer, side portions of the exterior member 2 are bonded by thermal welding or ultrasonic welding. With this configuration, one waist opening portion 4, into which a trunk of the wearer inserts, and two opening portions for inserting a leg 5, into which each leg of the wearer inserts, are formed at the disposable diaper 1.

As illustrated in FIG. 1 or 2, an end pressing sheet 18 is attached to the skin side surfaces of the front waist area 6 and the rear waist area 7. The end pressing sheet 18 is bonded to the skin side surface of the inner layer nonwoven fabric 21 with an adhesive (not illustrated). Upper surfaces of both ends of the absorbent body 3 in a longitudinal direction are covered with the end pressing sheet 18. Further, both ends of the outer layer nonwoven fabric 22 in the front and rear direction are folded back toward the skin surface side and bonded to the skin surface sides of the end pressing sheet 18.

A plurality of elastic members 11 extending in the widthwise direction are provided at the front waist area 6 and the rear waist area 7. For example, polyurethane rubber or natural rubber is used for the elastic member 11. The elastic member 11 is fixed between the inner layer nonwoven fabric 21 and the outer layer nonwoven fabric 22 with the adhesive (not illustrated).

At the time of manufacturing the disposable diaper 1, the elastic member 11 is attached between the inner layer nonwoven fabric 21 and the outer layer nonwoven fabric 22 in an extended state. As a result, the elastic member 11 shrinks the front waist area 6 and the rear waist area 7 in the widthwise direction. When the wearer wears the disposable diaper 1, the front waist area 6 and the rear waist area 7 are fitted to the waist of the wearer by shrinkage force of the elastic member 11.

Further, a plurality of elastic members 12a and 12b are provided at the front and rear of the opening portions for inserting a leg 5. The elastic members 12a and 12b, for example, are formed of polyurethane rubber, natural rubber, or the like. The elastic member 12a is disposed along forward edges of the pair of opening portions for inserting a leg 5, and is disposed so as to cross the crotch area 8 in the widthwise direction between the pair of opening portions for inserting a leg 5. Moreover, the elastic member 12b is disposed along rearward edges of the pair of opening portions for inserting a leg 5, and is disposed so as to cross the crotch area 8 in the widthwise direction between the pair of opening portions for inserting a leg 5. The elastic members 12a and 12b are fixed between the inner layer nonwoven fabric 21 and the outer layer nonwoven fabric 22 with the adhesive (not illustrated).

When manufacturing the disposable diaper 1, the elastic members 12a and 12b are attached in an extended state. As a result, the elastic members 12a and 12b shrink the edges of the opening portions for inserting a leg 5. When the wearer wears the disposable diaper 1, the edges of the opening portions for inserting a leg 5 are fitted to the leg perimeters of the wearer by shrinkage force of the elastic members 12a and 12b.

The absorbent body 3 is a part which is fitted to the crotch of the wearer and absorbs urine or the like discharged from a wearer. As illustrated in FIG. 3, the absorbent body 3 includes a liquid permeable top sheet 13 disposed on the skin side, a liquid impermeable back sheet 16 disposed on the outer side, and an absorbent core 19 interposed between the two sheets 13 and 16. Though the urine discharged from the wearer of the disposable diaper 1 passes through the top sheet 13, the urine does not penetrate to the outer side from the back sheet 16, and is absorbed and held by the absorbent core 19 between the top sheet 13 and the back sheet 16.

The top sheet 13, for example, is formed of a nonwoven fabric, in which a surface of a hydrophobic fiber (polypropylene, polyethylene, polyester, polyamide, nylon, or the like) is treated by surfactant and which becomes liquid permeable. However, a material of the top sheet 13 is not limited to this. For example, the top sheet 13 may be formed of a nonwoven fabric of a hydrophilic fiber (cellulose, rayon, cotton, or the like).

The absorbent core 19 is fixed between the top sheet 13 and the back sheet 16 with the adhesive (not illustrated). The absorbent core 19 of the present preferred embodiment is a mixture of a hydrophilic fiber, such as a crushed pulp fiber or a cellulose fiber, and granular Superabsorbent Polymer (SAP)

covered with a paper sheet, such as a tissue paper, or a permeable nonwoven sheet. However, a material or a structure of the absorbent core 19 is not limited to this. For example, the absorbent core 19 may be the one in which only Superabsorbent Polymer is molded into a sheet-like shape.

Further, the absorbent body 3 has a pair of side sheets 14 for preventing urine leakage toward the sides. The pair of side sheets 14, for example, is formed of a water-repellent nonwoven fabric such as a hydrophobic fiber (polypropylene, polyethylene, or the like).

The pair of side sheets 14 extends in the front and rear direction at both sides of the absorbent body 3. As illustrated in FIG. 3, the pair of side sheets 14 has a base end portion 14a bonded to the top sheet 13 and a standing portion 14b standing up relative to the base end portion 14a. The base end portion 14a is bonded to the skin side surface of the top sheet 13 with the adhesive (not illustrated). Only both ends of the standing portion 14b in the front and rear direction are fallen and fixed by the end pressing sheet 18.

A plurality of elastic members 15 for three-dimensional gathers extending in the front and rear direction are provided at the standing portion 14b. For example, polyurethane rubber or natural rubber is used for the elastic member 15 for three-dimensional gathers. When manufacturing the disposable diaper 1, the elastic member 15 for three-dimensional gathers is attached to the standing portion 14b of the side sheet 14 in a state in which the length is elongated from a natural length. As a result, the elastic member 15 for three-dimensional gathers shrinks the standing portion 14b of the side sheet 14 in the front and rear direction.

The absorbent body 3 is bonded to the skin side surface of the inner layer nonwoven fabric 21 with an adhesive 20. As illustrated in FIG. 3, the adhesive 20 is distributed below the absorbent body 3 in a vicinity of the center in the widthwise direction.

1.2. Method of Manufacturing the Pants Type Disposable Diaper 1

Next, a method of manufacturing the pants type disposable diaper 1 will be described.

Figure 4:
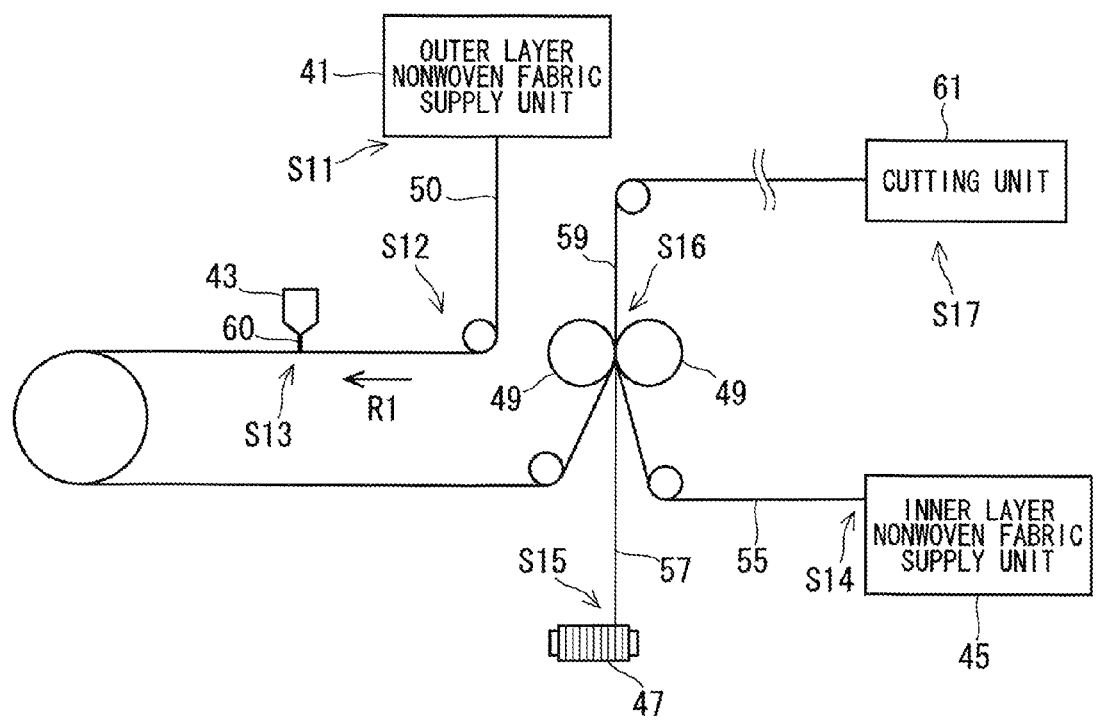
FIG. 4 is a diagram schematically illustrating a state in which the disposable diaper is manufactured on a manufacturing apparatus.

FIG. 4 is a diagram schematically illustrating a state in which the disposable diaper 1 is manufactured on a manufacturing apparatus. However, FIG. 4 mainly illustrates steps of bonding the outer layer nonwoven fabric 22 and the inner layer nonwoven fabric 21 with an adhesive 60.

An outer layer nonwoven fabric supply unit 41, for example, supplies an outer layer nonwoven fabric continuum 50 rolled in a roll shape (FIG. 4: step S11). The outer layer nonwoven fabric continuum 50 is a strip sheet which becomes the outer layer nonwoven fabric 22 after being cut. While a conveyance direction of the outer layer nonwoven fabric continuum 50 is appropriately changed by rollers provided here and there, the outer layer nonwoven fabric continuum 50 is conveyed to a pair of nip rollers 49, to be described below (FIG. 4: step S12). The outer layer nonwoven fabric continuum 50 is an example of a first sheet.

An application unit 43 for applying the adhesive 60 is disposed on a conveyance path of the outer layer nonwoven fabric continuum 50. The application unit 43 ejects an adhesive, which has been supplied from an adhesive supply source (not illustrated), from a plurality of ejection ports provided at a lower end of the application unit, and applies the adhesive 60 to an inner side surface (a surface opposing to the inner layer nonwoven fabric 21) of the outer layer nonwoven fabric continuum 50 (FIG. 4: step S13). An application step of the adhesive 60 to the outer layer nonwoven fabric continuum 50 in this step S13 will be described below in detail.

An inner layer nonwoven fabric supply unit 45, for example, supplies an inner layer nonwoven fabric continuum 55 rolled in a roll shape (FIG. 4: step S14). The inner layer nonwoven fabric continuum 55 is a strip sheet which becomes the inner layer nonwoven fabric 21 after being cut. Further, an elastic member supply unit 47 supplies an elastic member continuum 57 (FIG. 4: step S15). The inner layer nonwoven fabric continuum 55 is an example of a second sheet. The elastic member continuum 57 is a series of elastic members, which are disposed along the opening portions for inserting a leg 5 after being cut and serve as the elastic members 12a and 12b. Although illustration is omitted, it should be noted that an elastic member continuum, which is disposed along the waist opening portion 4 after being cut and becomes the elastic member 11, is also supplied in the same way as the elastic member continuum 57.

The outer layer nonwoven fabric continuum 50, to which the adhesive 60 has been applied, the inner layer nonwoven fabric continuum 55, and the elastic member continuum 57 are bonded by passing through between a pair of opposing nip rolls, thereby becoming an exterior member continuum 59 (FIG. 4: step S16). The exterior member continuum 59 is an example of a sheet-like base material.

Although illustration is omitted, after the absorbent body 3, the side sheets 14, the end pressing sheet 18, and the like are appropriately attached to a surface of the exterior member continuum 59, the exterior member continuum 59 is conveyed to a cutting unit 61. In the cutting unit 61, openings, which become the opening portions for inserting a leg 5, are formed at required positions of the exterior member continuum 59 by being cut by a cutter for leg holes (FIG. 4: step S17).

FIG. 5 is a schematic top view illustrating a state in which the adhesive 60 is applied to the outer layer nonwoven fabric continuum 50. As illustrated in FIG. 5, the application unit 43 is formed in an elongated shape along a direction orthogonal to a conveyance direction R1 of the outer layer nonwoven fabric continuum 50, and is divided into a three ejecting sections 431, 432, and 433 ejecting the adhesive 60. In FIG. 5, the ejecting sections 431, 432, and 433 are put together in one main body, however, they may be configured separately.

The adhesive 60 is independently supplied to each of the ejecting sections 431, 432, and 433. As a result, an on/off of the ejection of the adhesive 60 from the ejecting sections 431, 432, and 433 is controlled independently. The ejection control of this adhesive 60, for example, can be realized by respectively opening and closing a valve (electromagnetic valve or the like) mounted on each piping which connects the adhesive supply source and each of the ejecting sections 431, 432, and 433, based on a control signal from a control unit (not illustrated).

As illustrated in FIG. 5, an opening portion formation region 5R is divided into three regions (partial regions 51R, 52R, and 53R) by two straight lines L1 and L2, which are parallel to a conveyance direction R1 and pass an inside of the opening portion formation region 5R. These two straight lines L1 and L2 are respectively provided midway between the ejecting sections 431 and 433 and midway between the ejecting sections 432 and 433. The partial regions 51R, 52R, and 53R are respectively located below the ejecting sections 431, 432, and 433. The adhesive 60 ejected from the ejecting sections 431, 432, and 433 is respectively applied to the partial regions 51R, 52R, and 53R.

Figure 6A:
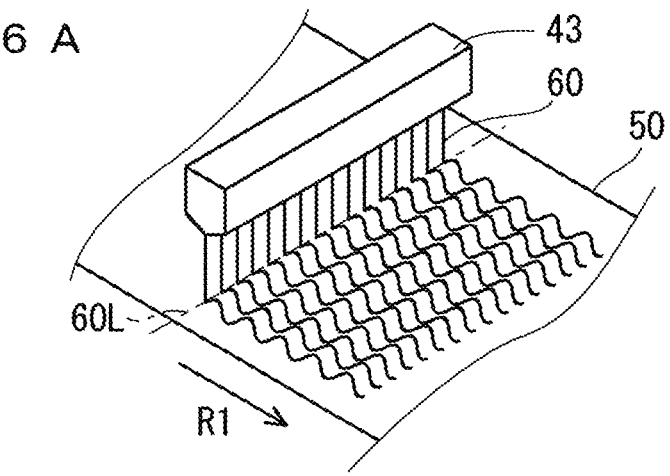
FIGS. 6A, 6B and 6C are schematic perspective views of an application unit ejecting the adhesive.
Figure 6B:
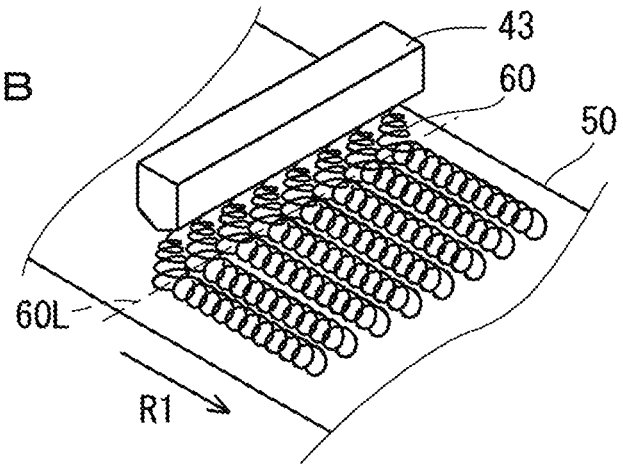
Figure 6C:
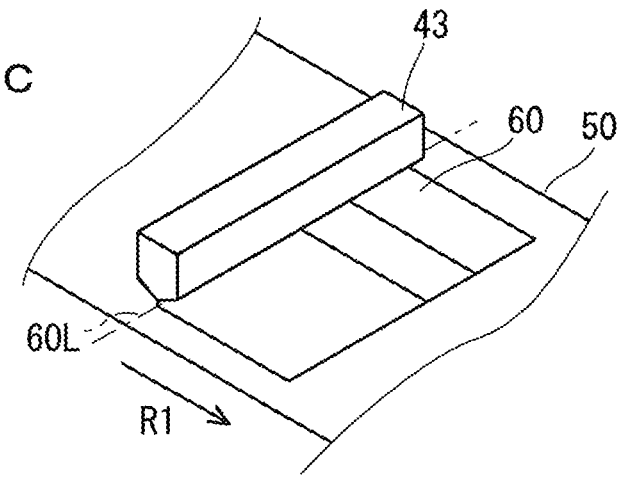

FIGS. 6A, 6B, and 6C are schematic perspective views of the application unit 43 ejecting the adhesive 60. FIG. 6A is a diagram illustrating a state in which the adhesive 60 is applied linearly to the outer layer nonwoven fabric continuum 50.

FIG. 6B is a diagram illustrating a state in which the adhesive 60 is applied spirally to the outer layer nonwoven fabric continuum 50. FIG. 6C is a diagram illustrating a state in which the adhesive 60 is applied in a planar state to the outer layer nonwoven fabric continuum 50.

When the adhesive 60 is applied linearly, the adhesive 60 is ejected from the plurality of ejection ports (not illustrated) formed at a lower part of the application unit 43. At this time, air is supplied to the ejected adhesive 60 from air supply ports provided front and behind a plurality of ejection ports with respect to the conveyance direction R1. With this configuration, as illustrated in FIG. 6A, since the adhesive 60 linearly drops from each of the plurality of ejection ports, the adhesive 60 is ejected from the respective ejecting sections 431, 432, and 433 like a curtain. Then, when the adhesive 60 is ejected from the ejecting sections 431, 432, and 433, the adhesive 60 is adhered to a predetermined position (position to be adhered 60L) on the outer layer nonwoven fabric continuum 50.

Further, as illustrated in FIG. 6B, when the adhesive 60 is applied spirally, the adhesive 60 is ejected from a plurality of ejection ports (not illustrated) formed at a lower part of the ejecting sections 431, 432, and 433. At this time, air is supplied to the ejected adhesive 60 from a plurality of (e.g., three to six) air supply ports provided around each ejection port at equal intervals. With this configuration, the dropping adhesive 60 rotates at high speed while being extended by the air supplied from each air supply unit and adheres to the outer layer nonwoven fabric continuum 50 while rotating spirally.

Moreover, as illustrated in FIG. 6C, when the adhesive 60 is applied in a planar state, the adhesive 60 is ejected from a slit-shaped ejection port formed at a lower part of the ejecting sections 431, 432, and 433. At this time, the slit-shaped ejection port is disposed at a position close to or a position abutting on the outer layer nonwoven fabric continuum 50. With this configuration, the adhesive 60 is applied to a surface of the outer layer nonwoven fabric continuum 50 (solid application).

When the adhesive 60 is applied linearly or spirally, a gap appropriate for adhesion between the outer layer nonwoven fabric continuum 50 and the inner layer nonwoven fabric continuum 55 can be formed. Accordingly, air permeability is satisfactorily secured. Further, when the adhesive 60 is applied in a planar state, the outer layer nonwoven fabric continuum 50 and the inner layer nonwoven fabric continuum 55 can be bonded uniformly.

Returning to FIG. 5, the ejecting sections 431 and 432 continuously eject the adhesive, as the outer layer nonwoven fabric continuum 50 moves in the conveyance direction R1. In contrast, the ejecting section 433 performs ejection of the adhesive 60 intermittently. More precisely, while the opening portion formation region 5R passes the position to be adhered 60L of the ejecting section 433, the ejecting section 433 stops ejection of the adhesive 60, and when the opening portion formation region 5R has passed the position to be adhered 60L of the ejecting section 433, the ejecting section 433 resumes the ejection of the adhesive 60. With this configuration, since the ejection of the adhesive 60 from the ejecting section 433 is performed intermittently, as illustrated in FIG. 5, a region in which adhesive application is not performed (referred "adhesive non-application region 531" hereinafter) is formed in the partial region 53R.

As described above, a part of the opening portion formation region 5R of the outer layer nonwoven fabric continuum 50 is cut and then discarded as a cut-out piece. Accordingly, the adhesive 60 applied to the opening portion formation region 5R becomes loss. In the present preferred embodiment, this opening portion formation region 5R is divided into three along the conveyance direction R1, and the adhesive 60 is applied thereto. By prohibiting the application of the adhesive 60 to the inner portion of the three divided portions, the loss of the adhesive 60 can be reduced.

It should be noted that, in the example illustrated in FIG. 5, the adhesive 60 is applied to the parts of the partial region 53R other than the adhesive non-application region 531 (both side parts of the adhesive non-application region 531). Further, the adhesive 60 is thoroughly applied to the partial regions 51R and 52R. Accordingly, the adhesive 60 is applied to the parts of the peripheral edge portions (boundary portions) of the opening portion formation region 5R, which are objects to be applied of the adhesive 60 by the ejecting sections 431, 432, and 433. Since the adhesive 60 is fully applied to the peripheral edge portions of the opening portion formation region 5R in this way, the peripheral edge portions of the outer layer nonwoven fabric continuum 50 and the inner layer nonwoven fabric continuum 55 can be bonded relatively firmly. As a result, cutting of the opening portion formation region 5R can be performed satisfactorily at the cutting unit 61. Moreover, the adhesive 60 for fixing the elastic member continuum 57 to the outer periphery of the opening portion formation region 5R is reliably applied.

It should be noted that the peripheral edge portion of the opening portion formation region 5R may have a part, to which the adhesive 60 is not applied. For example, ejection of the ejecting section 433 may be controlled in such a manner that the adhesive 60 is not applied to the entire partial region 53R. In other words, before the opening portion formation region 5R reaches the position to be adhered 60L, ejection of the adhesive 60 from the ejecting section 433 may be stopped temporarily, and after the opening portion formation region 5R passes the position to be adhered 60L, the ejection of the adhesive 60 from the ejecting section 433 may be resumed. In this case, the adhesive 60 is not applied to a part of the peripheral edge portion of the opening portion formation region 5R overlapping the peripheral edge portion of the inner partial region 53R. However, the amount of adhesive 60 to be used can be further suppressed. Therefore, the loss of the adhesive 60 can be further reduced.

It should be noted that a width W1 between the two straight lines L1 and L2, which pass the inside of the opening portion formation region 5R, can be changed arbitrarily. For example, when the width W1 between the two straight lines L1 and L2 is increased, a width of the adhesive non-application region 531 can be increased in a direction orthogonal to the conveyance direction R1. Here, by optimizing the width W1 between the two straight lines L1 and L2 according to a configuration of the opening portion formation region 5R, the loss of the adhesive 60 can be further reduced.

2. Second Preferred Embodiment

In the first preferred embodiment, the opening portion formation region 5R is divided into three partial regions 51R, 52R, and 53R, and the application of the adhesive 60 to the inner partial region held between the two outer partial regions of the three is prohibited, thereby forming the adhesive non-application region 531. However, it is possible to assume that the opening portion formation region 5R is divided more finely and the adhesive 60 is applied separately.

Figure 7:
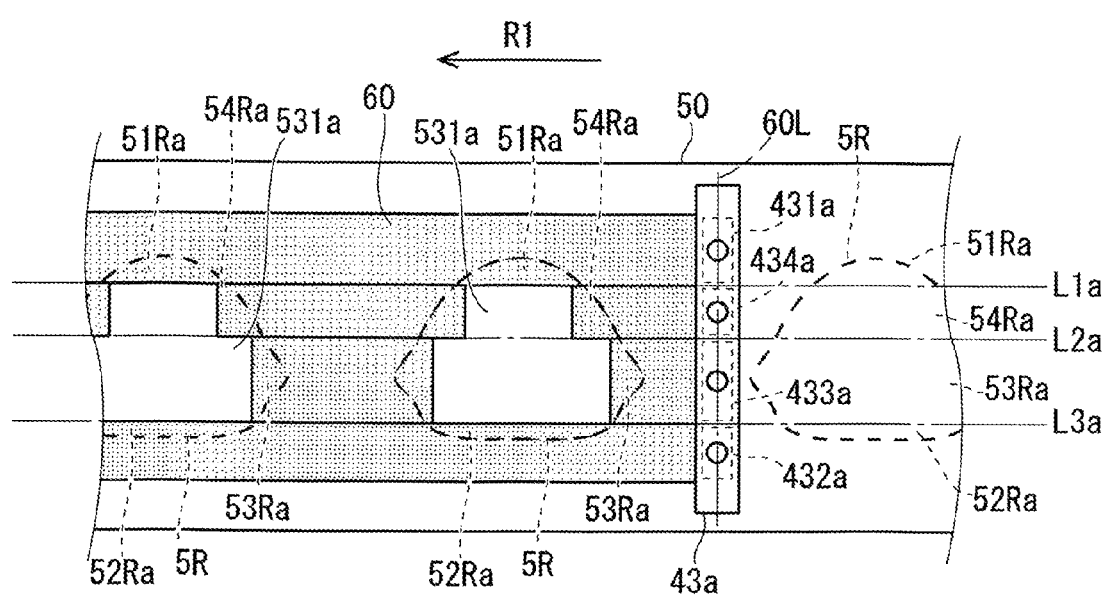
FIG. 7 is a schematic top view illustrating a state in which an adhesive is applied to an outer layer nonwoven fabric continuum in a second preferred embodiment.

FIG. 7 is a schematic top view illustrating a state in which an adhesive 60 is applied to an outer layer nonwoven fabric continuum 50 in a second preferred embodiment. As illustrated in FIG. 7, in the present preferred embodiment, an opening portion formation region 5R is divided into four partial regions 51Ra, 52Ra, 53Ra, and 54Ra by three straight lines L1a, L2a, and L3a, which are parallel in a conveyance direction R1. Additionally, an application unit 43a includes ejecting sections 431a, 432a, 433a, and 434a respectively corresponding to the partial regions 51Ra, 52Ra, 53Ra, and 54Ra, and is configured so as to eject and apply the adhesive 60 independently from these ejecting sections.

In the present preferred embodiment, the adhesive 60 is ejected continuously from the ejecting sections 431a and 432a corresponding to the outer partial regions 51Ra and 52Ra of the four partial regions 51Ra, 52Ra, 53Ra, and 54Ra. Accordingly, the adhesive 60 is thoroughly applied to the partial regions 51Ra and 52Ra. On the other hand, the adhesive 60 is intermittently ejected from the ejecting sections 433a and 434a. More precisely, the ejecting sections 433a and 434a temporarily stop ejection of the adhesive 60 after the opening portion formation region 5R reaches a position to be adhered 60L of each of the ejecting sections 433a and 434a, and the ejecting sections 433a and 434a resume the ejection of the adhesive 60 before the opening portion formation region 5R passes the position to be adhered 60L thereof. With this configuration, an adhesive non-application region 531 is formed over the partial regions 53Ra and 54Ra.

In this way, since the opening portion formation region 5R is divided more finely and the adhesive 60 is applied by the plurality of independent ejecting sections, the adhesive non-application region 531 is easily adjusted to the opening portion formation region 5R. Therefore, loss of the adhesive 60 can be further reduced.

It should be noted that when an area ratio of the adhesive non-application region 531 to the opening portion formation region 5R falls below 20%, the loss of the adhesive 60 becomes remarkable. For this reason, it is desirable that the adhesive 60 be applied in such a manner that the area ratio is greater than or equal to 20%. Further, in order to satisfactorily cut the opening portion formation region 5R in a cutting unit 61 and to reliably apply the adhesive 60 for fixing the elastic member continuum 57 to an outer periphery of the opening portion formation region 5R, it is desirable that the adhesive 60 be appropriately applied to a peripheral edge portion in such a manner that the above-described area ratio does not exceed 90%. Specifically, it is desirable that the adhesive 60 is applied from an edge portion of the opening portion formation region 5R to a part reaching an inside thereof by a predetermined degree (e.g., approximately 15 mm).

3. Variations

While preferred embodiments have been described above, the present invention is not limited by the above-description, and various modifications are possible.

For example, in the above-described preferred embodiments, the adhesive 60 is applied to the outer layer nonwoven fabric continuum 50. However, it can be assumed that the adhesive 60 is applied to the inner layer nonwoven fabric continuum 55.

Further, in the above-described preferred embodiments, the opening portion formation region 5R corresponds to the opening portion for inserting a leg 5. However, the opening portion formation region 5R may correspond to an opening portion provided for other uses.

Moreover, the pants type disposable diaper 1 described in the above preferred embodiments may be not only for adults but also for infants. Furthermore, the pants type disposable diaper 1 may absorb not only urine but also other excrement (body fluid), such as loose stools.

While the invention has been shown and described in detail, the foregoing description is in all aspects illustrative and not restrictive. It is therefore understood that numerous modifications and variations can be devised without departing from the scope of the invention.

What is claimed is:

1. A method of manufacturing a disposable diaper, comprising:
    (a) a step of conveying a first sheet in a predetermined conveyance direction;
    (b) a step of independently ejecting an adhesive from a plurality of ejecting sections and applying said adhesive to said first sheet conveyed in said (a) step;
    (c) a step of adhering a second sheet to a surface of said first sheet, to which said adhesive has been applied in said (b) step, and thereby forming a base material; and
    (d) a step of cutting said base material and forming an opening portion,
    wherein in said (b) step,
    the adhesive is ejected to three or more partial regions, of an opening portion formation region in which said opening portion is formed, which are divided by at least two or more straight lines passing an inside of the opening portion formation region from said ejecting sections corresponding to the partial regions,
    when ejection of said adhesive from said ejecting sections is stopped, an adhesive non-application region is formed in the one or more inner partial regions held between the outermost two partial regions of said three or more partial regions, and
    in said outermost two partial regions of said three or more partial regions, said adhesive is continuously ejected from said ejecting sections corresponding thereto.

2. The method of manufacturing a disposable diaper according to claim 1, wherein
    in said (b) step, said adhesive is applied linearly, spirally, or in a planar state.

3. The method of manufacturing a disposable diaper according to claim 1, wherein
    in said (b) step, said adhesive is applied in such a manner that an area ratio of said adhesive non-application region to said opening portion formation region does not exceed 90%.

* * * * *